United States Patent
Thomas et al.

(10) Patent No.: US 6,589,444 B2
(45) Date of Patent: Jul. 8, 2003

(54) PROCESS FOR SEPARATING WATER FROM CHEMICAL MIXTURES

(75) Inventors: Raymond Hilton Percival Thomas, Niagra County, NY (US); Roy Philip Robinson, Erie County, NY (US); David John Williams, Erie County, NY (US); Peter Brian Logsdon, Erie County, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/826,064

(22) Filed: Apr. 4, 2001

(65) Prior Publication Data

US 2001/0014707 A1 Aug. 16, 2001

Related U.S. Application Data

(63) Continuation of application No. 09/291,339, filed on Apr. 14, 1999, now abandoned, which is a continuation-in-part of application No. 08/967,632, filed on Nov. 10, 1997, now Pat. No. 6,101,818.
(60) Provisional application No. 60/112,546, filed on Dec. 16, 1998.

(51) Int. Cl.$^7$ .............................. B01J 20/18; B01J 20/26; C08J 9/22; C07C 17/389; F25B 47/00
(52) U.S. Cl. .................... 252/194; 210/689; 210/502.1; 62/85; 62/114; 62/475; 62/476; 521/52; 521/54; 521/99; 521/122; 521/123; 570/179; 570/262
(58) Field of Search .............................. 62/85, 475, 474, 62/476, 114; 210/689, 502.1, 637, 633; 570/262, 122, 177, 179; 252/194; 521/52, 54, 99, 122, 123

(56) References Cited

U.S. PATENT DOCUMENTS

| | | | |
|---|---|---|---|
| 3,446,645 A | 5/1969 | Drost ........................... 117/26 |
| 3,625,866 A | 12/1971 | Conde ..................... 252/455 Z |
| 4,013,566 A | 3/1977 | Taylor ......................... 210/502 |
| 4,144,171 A | 3/1979 | Krause ......................... 210/496 |
| 4,220,553 A | 9/1980 | Krause ......................... 252/428 |
| 4,266,408 A | 5/1981 | Krause .......................... 62/474 |
| 4,447,565 A | 5/1984 | Lula et al. ................... 523/219 |
| 4,777,232 A | 10/1988 | Heidel |
| 4,828,710 A | 5/1989 | Itoh |
| 4,985,467 A | 1/1991 | Kelly et al. .................... 521/52 |
| 5,069,816 A | 12/1991 | DeSantis et al. ......... 252/315.5 |
| 5,094,775 A | 3/1992 | Bailey, Jr. .............. 252/182.24 |
| 5,149,334 A | 9/1992 | Lahrman ..................... 604/367 |
| 5,191,771 A | 3/1993 | Meckler ....................... 62/271 |
| 5,198,121 A | 3/1993 | Masini ........................ 210/689 |
| 5,225,048 A | 7/1993 | Yuan ............................. 203/1 |
| 5,252,203 A | 10/1993 | Lyda |
| 5,297,398 A | 3/1994 | Meckler ....................... 62/271 |
| 5,347,822 A | 9/1994 | Lavin ............................ 62/85 |
| 5,440,898 A | 8/1995 | Starr ............................ 62/474 |
| 5,514,251 A | 5/1996 | Balthasart .................... 203/14 |
| 5,514,633 A | 5/1996 | Noguchi ....................... 502/64 |
| 5,534,186 A | 7/1996 | Walker et al. .............. 252/194 |
| 5,624,971 A | 4/1997 | Wilson ....................... 521/137 |
| 5,672,277 A | 9/1997 | Parker et al. ............... 210/689 |
| 5,719,201 A | 2/1998 | Wilson ....................... 521/137 |
| 6,020,281 A | * | 2/2000 | Lavin et al. .................. 502/68 |
| 6,101,818 A | * | 8/2000 | Thomas et al. ................ 62/85 |

FOREIGN PATENT DOCUMENTS

| | | |
|---|---|---|
| JP | 3093880 | 4/1991 |
| JP | 7033695 | 2/1995 |
| JP | 8173799 | 7/1996 |
| JP | 8206493 | 8/1996 |
| JP | 82006494 | 8/1996 |
| JP | 9241189 | 9/1997 |

OTHER PUBLICATIONS

Section Ch, Week 8301, Derwent Publications Ltd., London, GB, AN 83–00758K XP002090715 & JP 57 187306 A (Sumitomo Chem. Co. Ltd.) Nov. 18, 1982.

* cited by examiner

*Primary Examiner*—Joseph D. Anthony
(74) *Attorney, Agent, or Firm*—Deborah M. Chase; Colleen D. Szuch

(57) ABSTRACT

The present invention relates to novel compositions of drying agents of superabsorbent polymers, molecular sieves and mixtures thereof and binders of polyurethane foam, polyisocyanurate foam and supports comprising cellulose and a method for separating, drying and/or filtering chemical mixtures. The composition and method of the invention have broad applicability. They may be used for example to remove water from chemical mixtures like refrigerants (e.g., in vehicular refrigeration systems), air (e.g., in vehicular braking systems), natural gas and cleaning solvents (e.g., used in semiconductor manufacture and pipeline cleaning).

9 Claims, No Drawings

PROCESS FOR SEPARATING WATER FROM CHEMICAL MIXTURES

CROSS REFERENCE TO RELATED APPLICATIONS

This application is a continuation of U.S. patent application Ser. No. 09/291,339, filed Apr. 14, 1999 now abandoned, which is a continuation-in-part of U.S. patent application Ser. No. 08/967,632, filed Nov. 10, 1997, now U.S. Pat. No. 6,101,818, issued Aug. 15, 2000, which in turn, was based on Provisional Patent Application Serial No. 60/112,546 filed Dec. 16, 1998. The specifications of the above cross-referenced applications are hereby incorporated by reference in their entirety.

FIELD OF THE INVENTION

The present invention relates to novel desiccant compositions comprised of certain drying agents and binders and a method for separating, drying and/or filtering chemical mixtures. The composition and method of the invention have broad applicability. They may be used for example to remove water from chemical mixtures like refrigerants (e.g., in vehicular air conditioning systems), air (e.g, in vehicular braking systems), natural gas and cleaning solvents (e.g., in semiconductor manufacture and pipeline cleaning).

BACKGROUND OF THE INVENTION

A number of methods have been developed in order to separate water from chemical mixtures. The known methods include the use of alkaline earth compounds, carbon molecular sieves, oleum, distillation, and membranes. Many of the known methods are disadvantageous because the processes are inefficient or uneconomical; the drying agents undergo undesirable side reactions and/or adsorbs or absorbs the material being dried (See, U.S. Pat. No. 5,347,822).

Drying agents used principally in connection with circulating refrigerants include activated aluminum oxide, silica gels and molecular sieves in solid or granulated form. During use, these materials are abraded by the flow of the cooling liquid and mechanical vibrations and form dust particles. In order to prevent the dust from clogging the valves and conduits of the refrigeration system, a filter must be employed. This costs time (for installation) and money.

The compositions and method of the invention overcome the difficulties associated with the prior art. In particular, we have found that certain of the compositions eliminate the need for a separate filter element.

SUMMARY OF THE INVENTION

A composition comprising a drying agent and a binder wherein: (a) said drying agent comprises an effective amount of a molecular sieve and said binder comprises an effective amount of a support comprising cellulose; (b) said drying agent comprises an effective amount of a molecular sieve and said binder comprises at least about 25 weight percent of a material selected from the group consisting of polyurethane foam and polyisocyanurate foam; or (c) said drying agent comprises an effective amount of a superabsorbent polymer and molecular sieve and said binder comprises an effective amount of a material selected from the group consisting of polyurethane foam, polyisocyanurate foam and a support comprising cellulose.

A process comprising contacting a chemical mixture comprising water with an effective amount of a composition comprising a drying agent and a binder wherein: (a) said drying agent comprises an effective amount of a molecular sieve and said binder comprises an effective amount of a support comprising cellulose; (b) said drying agent comprises an effective amount of a molecular sieve and said binder comprises at least about 25 weight percent of a material selected from the group consisting of polyurethane foam and polyisocyanurate foam; or (c) said drying agent comprises an effective amount of a superabsorbent polymer and molecular sieve and said binder comprises an effective amount of a material selected from the group consisting of polyurethane foam, polyisocyanurate foam and a support comprising cellulose

DETAILED DESCRIPTION OF THE INVENTION

A. The Desiccant Composition

The invention relates to a desiccant composition comprising a drying agent and a binder. Specifically, the invention relates to the following compositions: A composition comprising a drying agent and a binder wherein: (a) said drying agent comprises an effective amount of a molecular sieve and said binder comprises an effective amount of a support comprising cellulose; (b) said drying agent comprises an effective amount of a molecular sieve and said binder comprises at least about 25 weight percent of a material selected from the group consisting of polyurethane foam and polyisocyanurate foam; or (c) said drying agent comprises an effective amount of a superabsorbent polymer and molecular sieve and said binder comprises an effective amount of a material selected from the group consisting of polyurethane foam, polyisocyanurate foam and a support comprising cellulose.

In another embodiment, the drying agent comprises an effective amount of a molecular sieve and said binder comprises from about 30 to about 75 weight percent of a material selected from the group consisting of polyurethane foam and polyisocyanurate foam.

In yet another embodiment, the drying agent comprises about 50 weight percent of a molecular sieve and said binder comprises from about 50 weight percent of a material selected from the group consisting of polyurethane foam and polyisocyanurate foam.

1. Drying Agent

For purposes of this invention the following terms have the indicated meanings: "Polymer" means a homopolymer, copolymer (not limited to only two components), or mixtures thereof having a molecular weight of from about 1,000,000 to about 100,000,000 and preferably from about 10,000,000 to about 100,000,000 and more preferably from about 85,000,000 to about 100,000,00 and which are crosslinked sufficiently to impart moisture absorbing or adsorbing properties; "Superabsorbent Polymer" means a Synthetic or Semi-Synthetic (defined below) Polymer that swells, to at least twice its dry volume, with the addition of water at room temperature after standing for up to two hours; Semi-Synthetic means a derivative of a naturally occurring Polymer; and "Synthetic" means a Polymer produced through chemical reaction.

Exemplary Semi-Synthetic Polymers include, without limitation, cellulose ethers, modified starches, starch derivatives, natural gum derivatives, and mixtures thereof. Illustrative Synthetic Polymers include, without limitation, polymers, related polymers, and polymer salts of acrylamide, acrylic acid, ethylene oxide, methacrylic acid, polyethyleneimine, polyvinyl alcohol, polyvinyl pyrrolidone, and mixtures thereof. For purposes of this invention "related polymer" means that the polymer repeat unit, or a branch thereof, is extended by carbon atoms, preferably from one to four carbon atoms. For example, a related polymer of acrylic acid is one in which the vinyl group is extended by one carbon to form an allyl group.

Synthetic Polymers are preferred. Polyacrylic acid and its salts are more preferred and sodium polyacrylate (such as SXM70 and SXM77 from Stockhausen of Greensboro, N.C.) and potassium polyacrylate are most preferred.

Any molecular sieve may be used in the composition of the invention. These materials are commercially available from for example UOP of Des Plaines, Ill. and Grace Corporation of Baltimore, Md. They may also be prepared by methods well known in the art. Suitable molecular sieves include without limitation: Type A, Type B, Type L, Type X, Type Y and mixtures thereof. In the practice of this invention Type A is preferred. For refrigeration applications molecular sieves of 3–4 Angstroms are preferred such as XH6, XH7, XH9 and XH11 from UOP.

Multiple drying agents may be used in the compositions and method of the invention. Besides Superabsorbent Polymers and molecular sieves, other known drying agents can optionally be employed in the compositions of the invention. They include without limitation activated alumina, activated carbon, silica gel and mixtures thereof. When multiple drying agents are used they may be used in any ratio that is from about 1 to about 99 to 99 to about 1.

The selection of drying agent(s) including type and form will depend on the process (including materials and equipment) that produces the chemical mixture or in which the chemical mixture is being used. The shape and hardness of the drying agent should be chosen to withstand the rigors of the system in which it is used and to avoid entrainment in the equipment, plugging openings and conduits. The drying agent may be a powder, fine particles, fibers, or a shaped piece or pieces. We have found that a 50/50 mixture of superabsorbent polymer and molecular sieve (with 50 weight percent binder) provides superior capacity and drying ability than either drying agent alone in a process for separating water from halogenated hydrocarbons, for example a refrigerant such as R-134a.

2. Binder

Any material capable of supporting the drying agent (including water absorbed/adsorbed in the drying agent) when may be used in the invention. Suitable binder materials include, without limitation, organic plastic binders such as isocyanate-based polymers, phenolic resins, aliphatic epoxy resins, silicone, polyvinyl alcohol resins, polyphenylene sulfide, poly(ether ketone), polyether sulfone, supports comprising cellulose and mixtures thereof. Polyurethane foam, polyisocyanurate foam and supports comprising cellulose are preferred. These materials are known in the art and can be purchased commercially or prepared by known methods. See, for example, U.S. Pat. Nos. 4,986,930, 4,655,757, 4,340,556, 4,596,567, 2,882,244, 2,950,952, 2,882,243 and 3,130,007 the disclosures of which are hereby incorporated by reference.

It is important to select a binder material that can be processed at a temperature that does not destroy the drying agent. In the case of thermoplastic binders, the processing temperature should be less than about 300° C., preferably less than about 250° C.

The desiccant compositions of the invention can be prepared by adding the drying agent as one of the components in the process (e.g, polymerization) used to prepare the binder. When a polyurethane foam or polyisocyanurate foam binder is used, the desiccant composition can be prepared by adding the drying agent with the other foam ingredients from the same or a different mix head and foaming the mixture. If a preblend of the foam ingredients is used, the drying agent can be added to the "A" and/or "B side" of the preblend. Preferably it is added to the "B side".

When cellulose is the binder, preferably, the desiccant composition has a laminate structure (i.e, layered e.g., binder/drying agent/binder etc.) Desiccant compositions which utilize a support comprising cellulose may be prepared by following the procedure outlined in European Patent Application 0 359 615.

The amount of drying agent and binder utilized in the desiccant composition is application dependent. Each should be used in "effective amounts" where this term means that amount of drying agent and optionally binder necessary to achieve a desired degree of dryness, separation and/or filtering and that amount of binder necessary to support the drying agent. This amount is readily determined by consideration of the amount of water sought to be separated, the flow rate of the chemical mixture, and the adsorptive or absorptive characteristics of the drying agent and binder. Generally, the desiccant compositions have the compositions disclosed in Table I below. The numerical ranges are understood to be prefaced by "about."

TABLE I

| Desiccant Composition | Range (wt. %) | Preferred Range (wt. %) | More Preferred Range (wt. %) | Most Preferred Range (wt. %) |
|---|---|---|---|---|
| Drying agent | 10–80 | 20–75 | 30–70 | 40–65 |
| Binder | 90–20 | 80–25 | 70–30 | 60–35 |

The requisite initial dryness of the drying agent will depend on such factors as the amount of water in the chemical mixture to be dried, the amount of drying agent used, and the equilibrium concentration of water in the drying agent when it is in contact with the chemical mixture at its final, or desired, water content. Preferably, the drying agent is dried to the greatest extent possible prior to. The temperature at which the drying agent is dried should be high enough to remove water without degrading the drying agent. In the case of molecular sieves this drying is conducted generally in a vacuum desiccator at temperatures up to 300° C. In the case of Superabsorbent Polymers the drying is conducted again in a vacuum desiccator but at temperatures between about 100 and 200° C. As the drying agent loses water, its weight decreases until it reaches a constant weight. At this point, the drying agent has been dried to the greatest extent possible at that particular temperature.

If the application requires that all but about 10 ppm or less of water be removed from the chemical mixture, it may be necessary to use an essentially anhydrous Water-Soluble Polymer. For purposes of this invention, "essentially anhydrous" means that the drying agent contains less than about 1 weight percent water.

B. Process

The amount of desiccant composition utilized will depend again on the application. An effective amount of the desiccant composition should be used where this term means an amount necessary to achieve a desired degree of dryness, separation and/or filtering. This amount is readily determined by consideration of the amount of water sought to be separated, the flow rate of the chemical mixture, and the adsorptive or absorptive characteristics of the drying agent and binder. Generally, the desiccant composition is used in an amount of from about 3 to about 700 percent, preferably from about 100 to about 700 percent and most preferably from about 200 to about 700 percent based upon the amount of water to be removed.

In another embodiment, the invention relates to a process comprising: contacting a chemical mixture comprising water with a drying effective amount of a desiccant composition comprising a drying agent and a binder wherein: (a) said drying agent comprises an effective amount of a molecular sieve and said binder comprises an effective amount of a support comprising cellulose; (b) said drying agent comprises an effective amount of a molecular sieve and said binder comprises at least about 25 weight percent of a material selected from the group consisting of polyurethane foam and polyisocyanurate foam; or (c) said drying agent comprises an effective amount of a superabsorbent polymer and molecular sieve and said binder comprises an effective amount of a material selected from the group consisting of polyurethane foam, polyisocyanurate foam and a support comprising cellulose.

For purposes of this invention, a chemical mixture is a liquid, gaseous or partially gaseous mixture of water and at least one inorganic material, organic material, or mixtures thereof. Illustrative inorganic materials include, without limitation, air, hydrogen, hydrogen chloride, sulfur dioxide, sulfur trioxide, carbon monoxide, carbon dioxide, boron trifluoride, uranium hexafluoride, sulfur hexafluoride, arsenic pentafluoride, halide salts, nitric acid, sulfuric acid, chlorine, metal ions, non-aqueous inorganic solvents, and mixtures thereof. Exemplary organic materials include, without limitation, alcohols such as methanol, ethanol and propanol, ketones including acetone, and aromatics including benzene, toluene and naphthalene, hydrocarbons, including gaseous hydrocarbons such as methane, ethane, propane and butane; and halogenated hydrocarbons such as chlorofluorocarbons, hydrochlorofluorocarbons, hydrofluorocarbons, and perfluorocarbons, chlorocarbons, hydrochlorocarbons, hydrofluoroethers, fluoroethers, and mixtures thereof, including without limitation difluoromethane, trifluoroethane, tetrafluoroethane, pentafluoroethane, pentafluoropropane and the like.

The process of the invention may be carried out in any suitable vessel. In the process of the invention, the chemical mixture is contacted with the desiccant composition for from about 1 to about 24 hours, preferably from about 1 to about 6 hours and most preferably from about 1 to about 4 hours.

In a particular application of the process embodiment, the desiccant composition is utilized in a refrigeration system such as a car air conditioning system to absorb water from the refrigerant. In this application, the process comprises cycling a refrigerant in a system wherein the refrigerant is condensed and thereafter evaporated, said system comprising an effective amount of a composition comprising an drying agent and a binder wherein said drying agent comprises an effective amount of a material selected from the group consisting of superabsorbent polymer, molecular sieve and mixtures thereof and said binder comprises an effective amount of a material selected from the group consisting of polyurethane foam and polyisocyanurate foam and a support comprising cellulose.

In this application, the desiccant composition may comprise the core of a drier. A drier core which utilizes a drying agent of the invention with a polyurethane foam or polyisocyanurate foam binder, may be prepared by adding the drying agent to a foam formulation in the manner discussed above and foaming the composition in a container, the resulting desiccant composition would comprise the core and the container the drier. A drier core which utilizes a drying agent of the invention and a support comprising cellulose as the binder, can be prepared by adding the drying agent to the cellulose binder as discussed above and rolling or stacking the resulting composition in a container. The desiccant composition would once again comprise the core and the container the drier. This drier core would be fixed in the refrigeration system in the circulation path by means known in the art.

Applicants have discovered that a desiccant compositions comprising a mixture of a Superabsorbent Polymer and molecular sieve and a polyurethane or polyisocyanurate foam binder are particularly useful in this process embodiment especially at loadings of about 50 weight percent drying agent (50:50 ratio of drying agents) and 50 weight percent foam. This composition exhibits several advantages over prior art materials including greater capacity and drying ability, smaller volume and elimination of a separate filter element.

In another application of the process of the invention, the invention can be used to absorb water from spent cleaning solvent such as that used in semiconductor manufacture or natural gas or other pipeline cleaning. The process would comprise exposing a solvent comprising water to a desiccant composition of the invention. This could be done after the solvent was recovered as a separate step or during the cleaning process itself. In the latter application, the desiccant composition would be fixed, for example, to the inside of a pipeline and the solvent in the course of passing through the pipeline would pass through the desiccant and water would be removed from the solvent. In still another application of the process of the invention, the invention can be used to absorb water from air such as for example in air brake applications.

In all embodiments, the performance of the drying agent may be improved by periodically regenerating the drying agent to release the water separated from the chemical mixture. Regeneration may be accomplished by any convenient means, such as by heating the drying agent to a temperature suitable to release water from the drying agent.

The amount of water removed by the Superabsorbent Polymer must be monitored in order to maintain its mechanical integrity. If the Superabsorbent Polymer is in solid form, allowing the amount of water separated from the chemical mixture by the Superabsorbent Polymer to reach a level at which it turns from a solid into a gel or liquid may be disadvantageous. The amount of water at which this phase change occurs will vary depending on the Superabsorbent Polymer used but is readily determined by routine experimentation. Preferably, the Superabsorbent Polymer is used to a point just below the point at which a phase change occurs. Water separation may be monitored by any convenient means as for example, measuring the amount of water in the chemical mixtures. Further, if one or more other chemicals in the chemical mixture forms a gel or solid with the Superabsorbent Polymer, the water required for the solid to liquid phase change may be altered.

If very low levels of water are desired in the chemical mixture, that mixture may be treated sequentially with more than one drying agent bed to reach the desired level. We have discovered the use of a sodium polyacrylate polymer bed followed by a molecular sieve bed is particularly effective. Alternatively, the process of the invention may be used in conjunction with other well known drying methods.

The invention will be clarified further by a consideration of the following examples, which are purely exemplary.

EXAMPLES

Example 1

This example demonstrates the preparation of a desiccant composition comprising polyurethane foam and a superabsorbent polymer. The isocyanate or A component of the mixture used was Mondur 2OS available from Bayer Corporation. The formulation of the B component of the mixture was as follows:

- 50 parts VORANOL-490 (polyol available from Dow Chemical Co.)
- 50 parts VORANOL-391 (polyol available from Dow Chemical Co.)
- 2.5 parts L-6164 (surfactant available from Goldschmidt Chemical Co.)
- 3.2 parts POLYCAT 41 (catalyst available from Air Products and Chemicals)
- 53 parts HCFC-141b (blowing agent available from AlliedSignal Inc.).

The A and B side were mixed together and sodium polyacrylate (constituting 43 weight percent of the entire mixture) was added to the mixture and quickly stirred. The whole mass was then poured into a 150 cc Teflon vessel. The vessel was capped and the foam allowed to rise. The vessel was equipped with ports on both ends so that gaseous refrigerant could be passed through it.

Example 2

A sample of R-134a containing 578 ppm water was passed through the vessel described in Example 1 above which contained 27 grams of the potassium salt of polyacrylic acid and foam (The potassium salt of polyacrylic acid comprised 43% of the composition). The moisture content on exiting the vessel was measured using a Karl Fischer coulometer and found to be 25 ppm.

Example 3

The experiment of Example 2 is repeated except that R-134a containing 1114 ppm water was passed through a different vessel containing 51.3 grams of the desiccant composition (containing 43% of the potassium salt of polyacrylic acid). The moisture content on exiting the vessel was 23 ppm.

Example 4

A desiccant composition was prepared as in Example 1 except that the sodium polyacrylate constituted 70 weight percent of a 30 gram sample. Wet nitrogen was passed through the vessel until the desiccant composition had absorbed 20% of its dry weight in water. R-134a was then passed through the vessel very slowly. The exiting R-134a had a moisture content of about 180 ppm. This example demonstrates the superior capacity of the desiccant composition in that even after having absorbed 20% of its dry weight in water, the moisture concentration is far below that reported in the 1994 ASHRAE Handbook for molecular sieve (800 ppm at 16% of its dry weight in water). (I do not understand this)

Example 5

A desiccant composition is prepared as in Example 1 except that the polyol used is polybutylene oxide and the sodium polyacrylate constitutes 60 weight percent of a 30 gram sample. Wet nitrogen is passed through the vessel until the desiccant composition absorbs 20% of its dry weight in water. R-134a is passed through the vessel very slowly. The exiting R-134a has a moisture content of about 180 ppm.

Example 6

A desiccant composition is prepared as in Example 1 except that the polyol used is polypropylene oxide and the sodium polyacrylate is about 60 weight percent of a 30 gram sample. R-134a is passed through the vessel very slowly. The exiting R-134a has a moisture content of about 180 ppm.

Example 7

Sodium polyacrylate deposited on cellulosic material was obtained from Gelok International. The material's tradename is 9525 s/s. A strip that measured 16 in.×2 in. was rolled to fit into a stainless steel cylinder that was 11.5 in. tall with a diameter of 1.5 in. The cylinder was initially open at both ends. Two ends with tube connection were then bolted on to the cylinder. This fixture was then connected to an apparatus comprising a pump, a supply cylinder of dry R-134a, a flow meter and a loop that bypassed the fixture. The loop contained Celite that was saturated with water. A Panometrics MIS2 probe for measuring the moisture in liquid refrigerants was attached in line with the fixture. The apparatus, with the refrigerant supply cylinder valves closed, was evacuated. The valves were then opened and liquid refrigerant fed to the pump and the pump turned on. In order to wet the refrigerant, the fixture was closed off and the refrigerant fed through the bypass loop. The bypass was then closed and the fixture opened. The reading on the probe was initially off scale indicating a very high moisture level. After a few minutes the probe registered 380 ppm. After three hours the concentration of water in the R-134a was measured to be 100 ppm.

Example 8

A rigid, open-celled foam was blown into a cylinder that was 4 in. long and 1.5 in. in diameter. The foam formulation contained a mixture of sodium polyacrylate and molecular sieve (7.25 grams each). The cylinder was initially open at both ends. Two ends with tube connection were then bolted on to the cylinder. This fixture was then connected to an apparatus comprising a pump, a supply cylinder of dry R-134a, a flow meter and a loop that bypassed the fixture. The loop contained Celite that was saturated with water. A Panometrics MIS2 probe for measuring the moisture in liquid refrigerants was attached in line with the fixture. The apparatus, with the refrigerant supply cylinder valves closed, was evacuated. The valves were then opened and liquid refrigerant fed to the pump and the pump turned on. In order to wet the refrigerant, the fixture was closed off and the refrigerant fed through the bypass loop. The bypass was then closed and the fixture opened. The reading on the probe was initially off scale indicating a very high moisture level. After 6 minutes the probe registered 528 ppm. After 50 minutes the concentration of water in the R-134a was measured to be 86 ppm.

What is claimed is:

1. A desiccant composition comprising:
   a drying agent comprising an effective amount of a superabsorbent polymer and molecular sieve; and
   a binder comprising an effective amount of a material selected from the group consisting of polyurethane foam and polyisocyanurate foam.

2. The composition of claim 1 wherein said superabsorbent polymer comprises sodium polyacrylate or potassium polyacrylate.

3. The composition of claim 1 wherein said binder comprises polyurethane foam.

4. The composition of claim 1 wherein said binder comprises polyisocyanurate foam.

5. The composition of claim 1 wherein said composition further comprises at least one drying agent selected from the group consisting of activated alumina, activated carbon and silica gel.

6. A drier core comprising an effective amount of a desiccant composition comprising: a drying agent comprising an effective amount of a superabsorbent polymer and molecular sieve; and a binder comprising an effective amount of a material selected from the group consisting of polyurethane foam and polyisocyanurate foam.

7. The drier core of claim 6 wherein said drying agent is present in an amount of from about 10 to about 80 weight percent and said binder is present in an amount of from about 20 to about 90 weight percent.

8. The drier core of claim 6 wherein said superabsorbent polymer comprises sodium polyacrylate or potassium polyacrylate.

9. The drier core of claim 6 wherein the drying agent further comprises at least one drying agent selected from the group consisting of activated alumina, activated carbon and silica gel.

* * * * *